(12) United States Patent
Gemunder et al.

(10) Patent No.: US 6,798,396 B2
(45) Date of Patent: Sep. 28, 2004

(54) FOOT SWITCH INTERFACE FOR OPERATION OF COMPUTER

(75) Inventors: Elliot R. Gemunder, Dix Hills, NY (US); Jeff Nagel, Nesconset, NY (US)

(73) Assignee: Air Techniques, Inc., Hicksville, NY (US)

( * ) Notice: Subject to any disclaimer, the term of this patent is extended or adjusted under 35 U.S.C. 154(b) by 258 days.

(21) Appl. No.: 09/790,238

(22) Filed: Feb. 21, 2001

(65) Prior Publication Data

US 2002/0030661 A1 Mar. 14, 2002

Related U.S. Application Data

(60) Provisional application No. 60/184,034, filed on Feb. 22, 2000.

(51) Int. Cl.[7] .................................................. G09G 5/00
(52) U.S. Cl. ........................ 345/156; 345/160; 345/168
(58) Field of Search ................................ 345/163, 160, 345/167, 157, 168; 433/28

(56) References Cited

U.S. PATENT DOCUMENTS

| | | | | | |
|---|---|---|---|---|---|
| 5,334,997 | A | * | 8/1994 | Scallon | 345/167 |
| 5,838,305 | A | * | 11/1998 | Bookstein | 345/163 |
| 5,889,510 | A | * | 3/1999 | Klarlund | 345/168 |
| 5,907,318 | A | * | 5/1999 | Medina | 345/163 |
| 5,931,669 | A | * | 8/1999 | Fornoff et al. | 433/28 |

FOREIGN PATENT DOCUMENTS

GB          2338052 A    * 12/1999     ............. G06F/3/02

* cited by examiner

*Primary Examiner*—Steven Saras
*Assistant Examiner*—Fritz Alphonse
(74) *Attorney, Agent, or Firm*—Louis E. Marn; Clifford G. Frayne

(57) ABSTRACT

A foot switch, interface and associated software, the foot switch having a plurality of switch positions and which permits the operator to duplicate the equivalent series of keyboard entries for the operation of computer functions by means of foot manipulation utilizing the foot switch.

8 Claims, 3 Drawing Sheets

FUNCTIONS AND KEYSTROKES USED IN THE PRE-PROGRAMMED SOFTWARE

Dentrix

| FUNCTION | KEYSTROKES SAVED |
|---|---|
| Freeze | ALT f ALT |
| Unfreeze | ALT f ALT |
| Capture | ALT c ALT |
| Exit | ALT x ALT ALT a ALT y |
| Print | ALT i ALT p p |

Eaglesoft

| FUNCTION | KEYSTROKES SAVED |
|---|---|
| Freeze | ALT f ALT |
| Unfreeze | ALT u ALT |
| Save | ALT s ALT |
| Cancel | ALT c ALT |
| Print | ALT s ALT ALT p ALT i ALT ALT o ALT |

Vipersoft

| FUNCTION | KEYSTROKES SAVED |
|---|---|
| Capture | ALT c ALT |
| Retake | ALT r ALT |
| Go live/Save | ALT s ALT ALT g ALT |
| Done | ALT d ALT ALT i ALT a |
| Print | ALT p ALT y ENT |

FIG. 3

FOOT SWITCH INTERFACE FOR OPERATION OF COMPUTER

This application claims benefit of 60/184,034 filed Feb. 22, 2000.

BACKGROUND OF THE INVENTION

1. Field of the Invention

The present invention relates to a foot switch control and interface permitting the operation of a computer by manipulating the foot switch control with one's foot. While the present invention has general application to the operation and control of a computer, it finds particular application in medical or dental situations wherein certain procedures or diagnostics are performed with the aid of computer and there is a need to prevent cross contamination from patient to patient as a result of the medical professional contacting a computer keyboard or computer mouse during the procedure.

2. Background of the Invention

The foot switch control and interface of the present invention can have general application to the operation of a computer and allows the operator to duplicate keyboard entries which would normally be made by the hands of the operator. The foot switch and interface of the present invention allows for the operation of the computer by the operator's foot and allows the operator's hands to be free for performing other tasks. It has particular advantage in dental and medical arts where procedures and diagnostics are performed on an individual with the aid of a computer. The medical or dental professional has his or her hands free for performing the procedure or diagnostic, but can still manipulate the computer with their foot.

The dental arts has progressed from the well-known x-ray system in which multiple x-rays of the mouth were obtained and mounted on x-ray cards in the patients's paper file, to advanced oral video systems in which the oral cavity and dental procedures conducted within the oral cavity are filmed and stored in a computer database for subsequent review or viewing. The central processing unit of the computer is equipped with a video capture card which allows the image to be stored in the computer data base and viewed on the computer monitor by the dentist or patient when desired.

The video capture card and associated software allow the dentist, or dental technician to store the images and to manipulate the images on the computer screen by means of the computer keyboard or a computer mouse. The images, either still or video are capable of being captured, stored and printed. A problem which has arisen is that the dentist or dental technician when capturing, storing, manipulating or printing an image, must necessarily come in hand contact with either the computer keyboard or the mouse and since the capturing and manipulating of an image can be occurring simultaneously with the dental procedure being conducted within the oral cavity, the computer keyboard or mouse is subject to patient cross contamination and/or asepsis even though the dentist or dental technician is wearing protective gloves.

There is therefore a need to allow or permit the dentist or dental technician to capture, store, manipulate or print the images while actually performing the dental procedure such that no patient cross contamination can occur between patients. Since many of the operations of a dental chair are controlled by foot pedals or foot switches, a dentist or dental technician is comfortable and adept in the operation of such foot switch or foot pedal and the present invention relates to a foot switch and interface which permits the dentist or dental technician to operate the computer and imaging system by manipulation of a foot so as to prevent patient; cross contamination and asepsis and still allow the dentist or dental technician to perform the necessary, and equivalent programmed keyboard functions and entries to capture, store, manipulate and print the images.

SUMMARY OF THE INVENTION

A foot switch, interface and associated software, the foot switch having a plurality of switch positions and which permits the operator to duplicate the equivalent series of keyboard entries for the operation of computer functions by means of foot manipulation utilizing the foot switch. In a preferred embodiment, the manual keyboard and the foot switch would be connected in parallel to an interface which in turn would be in communication with the central processing unit. In the context of the dental arts, when there is no dental procedure being performed and hence no danger of patient cross contamination, the manual manipulation of the keyboard can manipulate the central processing unit. When computer use is required while a dental procedure is being performed simultaneously, the operator can control the computer functions from the foot switch which in cooperation with the interface and the associated software would duplicate the keyboard entries of the computer keyboard and operate the computer.

OBJECTS OF THE INVENTION

An object of the present invention is to provide for a novel programmable foot switch control for operation of a computer.

A further object of the present invention is to provide for a novel programmable foot switch control which duplicates the series of keyboard entries currently utilized to operate or initiate computer functions.

A still further object of the present invention is to provide for a novel programmable foot switch control for a dental imaging system which eliminates the possibility of asepsis and patient cross contamination by eliminating contact with the computer keyboard or computer mouse during the process of capturing, storing, manipulating or printing an image during the course of a dental procedure.

BRIEF DESCRIPTION OF THE DRAWINGS

These and other objects of the present invention will become apparent particularly when taken in light of the following illustrations wherein:

FIG. 3 is a diagram of the foot switch functions in comparison to the duplicate keyboard entries.

DETAILED DESCRIPTION OF THE DRAWINGS

Figure 1:
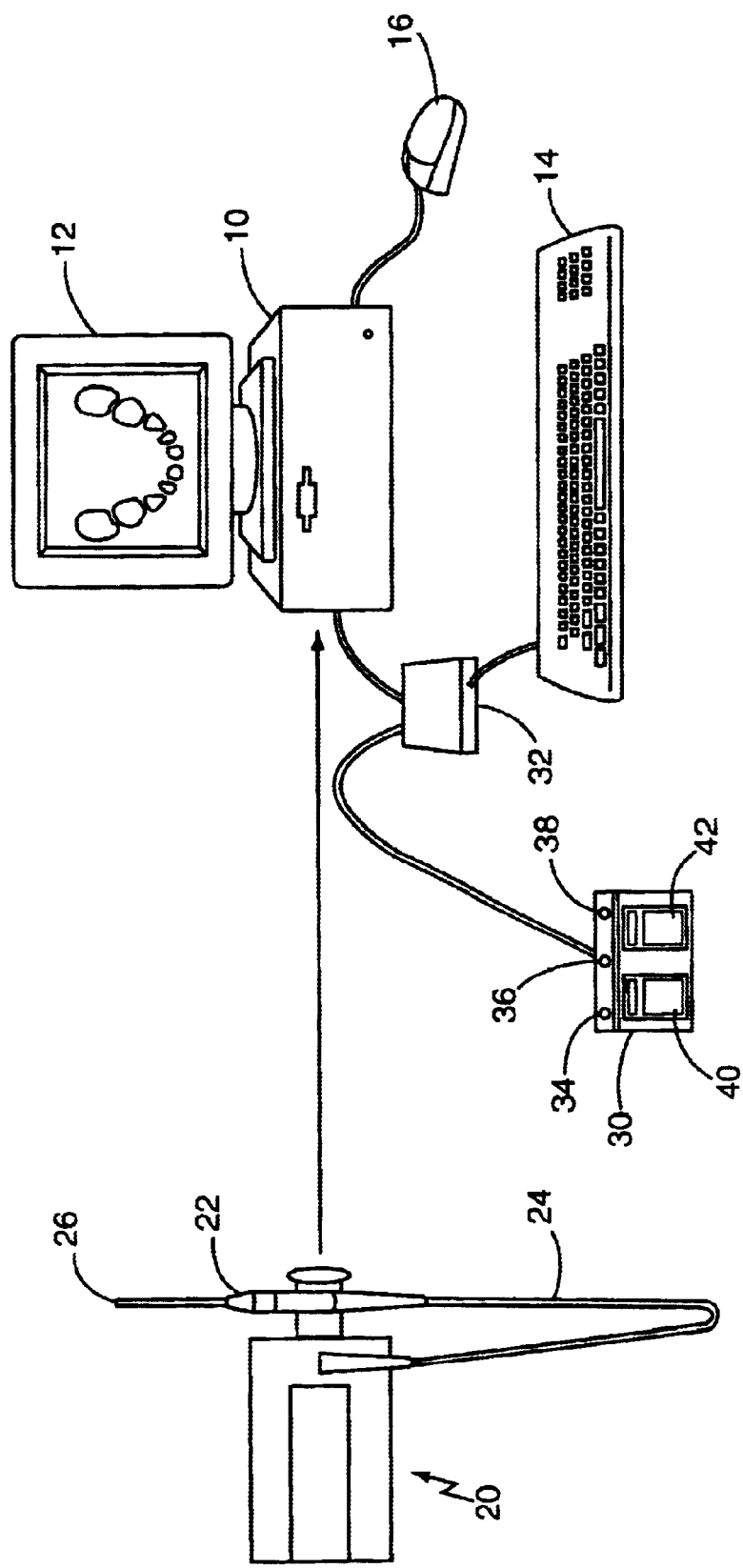
FIG. 1 is a schematic diagram of a dental imaging system utilizing a foot switch of the present invention.

FIG. 1 is a schematic diagram of a dental imaging system which will be utilized to explain the novelty and benefits of the, foot switch interface in a dental imaging procedure. A typical computer comprising a central processing unit or CPU 10, a monitor 12, a keyboard 14, and a mouse 16, would be utilized to store, manipulate, view or print dental images.

The dental images of the oral cavity would be photographed by the dentist or dental technician using a specialized camera 20 which would have the ability to view and image selected portions of the oral cavity by means of a hand piece 22, light guide 24 and lens 26. The image generated by camera. 20 is digitally communicated to the central processing unit 10 which is equipped with a video capture card (not shown) which digitally stores the images.

The dentist may be using one of several operating programs within the central processing unit. These may include Dentrix, Eaglesoft, or Vipersoft, or any other similar software program. Each of these programs operate with drop down menus on the monitor 12 which utilize a variety of keyboard short cuts which are initiated by key stroke commands from the keyboard 14. Applicant's foot switch, interface and software allows the dentist to duplicate the short cut keystroke commands by way of the foot switch as described hereafter.

The dentist or dental technician can establish his file paths for the images by means of the keyboard 14 or mouse 16 prior to commencing a dental procedure, and can view the images on the monitor 12 on a large scale. Further, the images can be stored and brought up for later review or illustration to the patient by means of the keyboard 14 or mouse 16 functions.

The problem which Applicant seeks to solve arises when the dentist or dental technician needs to view or manipulate images or perform a computer function while performing a dental procedure. Manipulation of a client's file or images would require the dentist or dental technician to come into contact with the keyboard in order to execute certain functions. While the dentist or dental technician may be wearing latex gloves, the saliva or blood which may have contacted the latex gloves as the result of performing a dental procedure would necessarily come in contact with the keyboard when manipulating files or images via keyboard functions. The dentist or dental technician may change latex gloves between patients, but nevertheless, there is a contamination of the keyboard which cannot be easily remedied. The foot switch and interface eliminates the possibility of cross contamination between patients by allowing the dentist or dental technician to perform the necessary keyboard functions to either store, manipulate, view or print images by using the foot switch 30 and foot switch interface 32 which allows for the duplication of keyboard functions.

In the preferred embodiment, the keyboard 14 and foot switch 30 would be connected in parallel through the interface 32 to the computer through the central processing unit 10. The foot switch 30 would have five switch members 34, 36, 38, 40 and 42 positioned so that they could be individually engageable by the toe portion or the foot. (See FIG. 2). The foot switch 30, interface 32, and associated software permit the programming of 24 key stroke commands for each, of the five switch locations. Once programmed, the keystroke commands are committed to memory until it is desired to reprogram the functions and the key stroke commands would automatically perform the programmed function once selected switch members 34 and 42 was depressed.

Figure 2:
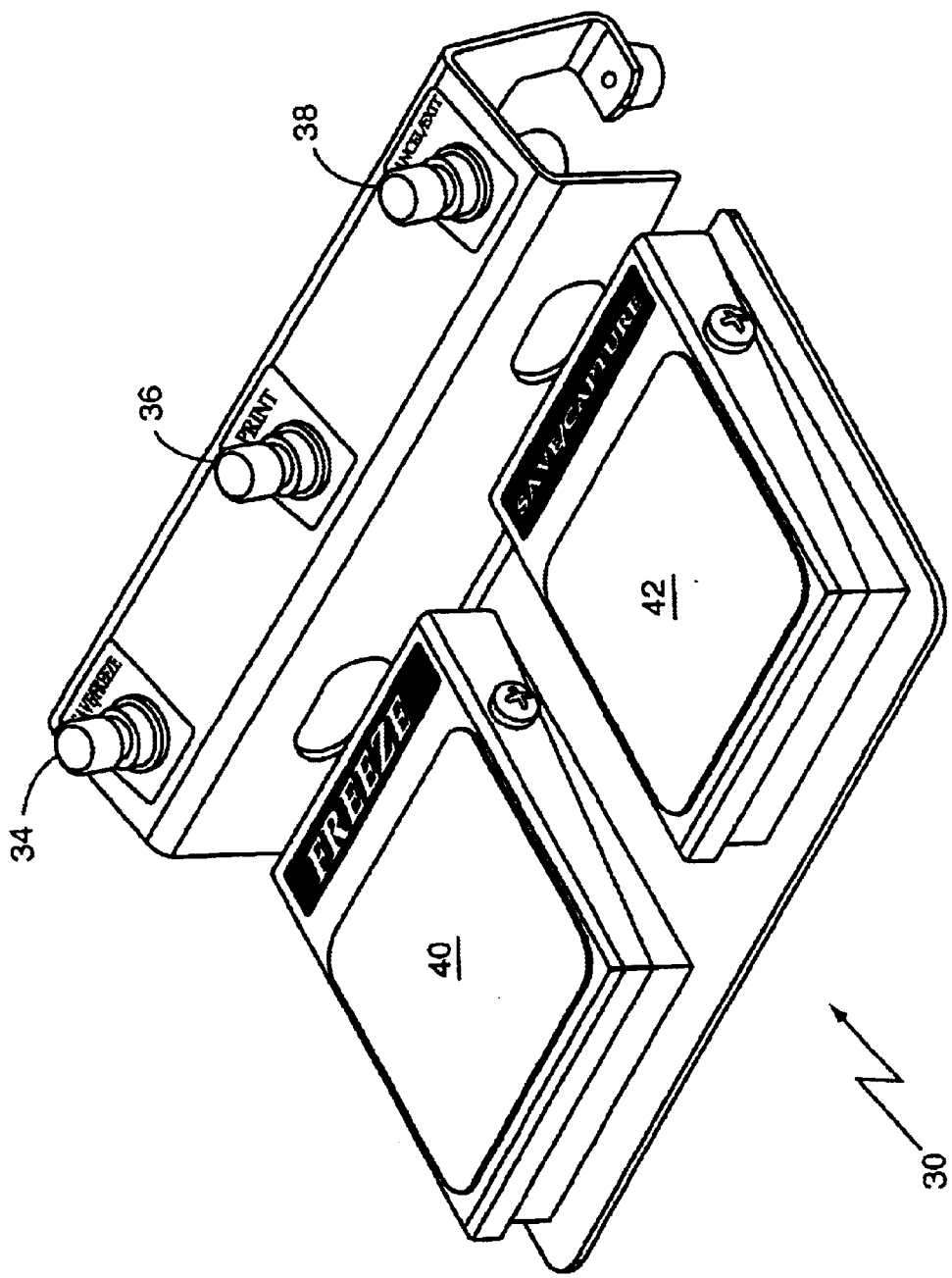
FIG. 2 is a top view of the foot switch of the present invention.

FIG. 2 is a top view of the foot switch 30 which illustrates the positioning of the five distinct switches 34, 36, 38, 40 and 42, which would be activated by the foot of the dentist or dental technician. In-this manner, the dentist or dental technician can perform dental procedures within the oral cavity and simultaneously control the imaging which appears on the monitor without having to manually contact the keyboard and thus avoid the possibility of cross contamination between patients.

In FIG. 2, the five distinct switches have been labeled to indicate the functions which have been programmed into each switch and which will perform a computer function of up to 24 distinct keystroke commands. In this example, switch 34 is labeled unfreeze; switch 36 is labeled print; switch 38 is labeled cancel/exit; switch 40 is labeled freeze; and switch 42 is labeled save/capture.

In performing the oral imaging, the dentist or dental technician could activate switch 42 to save and capture the particular image in computer memory. This image could subsequently be printed by activating switch 36. Still further, in the course of performing the dental imaging, the dentist or dental technician could freeze the image on the screen by activating switch 40 and unswitch the image by activating switch 34. The particular function or program could be canceled or exited by activating switch 38.

The program allows the dentist or dental technician to change or modify the particular function associated with each switch and thus relabel the switch for a program or function of choice. Further, the switches 34 through 42 could be relabeled depending upon which program, Dentrix, Eaglesoft, or Vipersoft or other similar software programs the dentist is utilizing in the central processing unit 10.

The foot switch interface can store up to 24 keystroke commands for each switch positioned on the foot switch. Once programmed, it remains memorized until changed or reprogrammed. The keyboard entries that can be duplicated by the foot switch are the "keyboard shortcuts" identified by an underlined letter on the pull down menu on the computer video monitor depending upon which program the dentist is utilizing in the central processing unit 10. As an example, the function "Freeze" would be executed by the keyboard shortcut ALT F ALT. The underlined letter in the function is the keyboard shortcut and is activated by pressing the "ALT" key. Certain keys generate two separate key strokes each time they are depressed and released. One key stroke is generated with the key is depressed and another when the key is released. Therefore when one of these keys is used with an associated letter three key strokes are generated and must be saved in memory thereby reducing the 24 key stroke memory per switch by 3 key strokes.

If the dentist wishes to custom program the foot switch interface,the dentist must first determine which commands he wants to program and write them down in the sequence to be executed. These steps can then be committed to memory and assigned to a particular switch 34–42 by the following sequence.

1. Run the VistaCam PC Footswitch configuration program as follows:
   a. Double click on the VistaCam Footswitch icon in the desktop, or
   b. Click on the Start button.
   C. Click on Programs.
   d. Click on VistaCam PC FS Interface.
   e. Click on VistaCam PC FS Interface.
2. Clear each switch prior to programming it as follows:
   a. Click on CLEAR SW# or CLR #.(replace # with the switch number).
   b. All the previously stored information displayed in the associated switch's box will be erased.
3. To program a switch click on the button for that switch (SWITCH # or SW #). The box that displays the stored keystrokes will turn white and be ready to accept new keystroke information.
4. Refer to the commands that you previously wrote down on paper and type the keystrokes you want stored in that switch.

When programming the cursor keys (arrows), if the Num Lock is on when you program the cursor keys, then it must be on when you go to use that switch. If the Num Lock is off when you program the cursor keys, then it must be off when you go to use that switch.

5. Repeat steps 2–4 for each of the five switches.
6. To save your settings (for later recall), do the following:
   a. Click the SAVE button.
   b. Type a name you want to save your program as (up to eight characters)c.
   c. Click the ENTER button.
7. Click the CONFIGURE button to enter your program settings into the VistaCam PC Footswitch Interface. These setting will remain stored in the VistaCam PC Footswitch Interface until changed as described above.
8. To recall and use your previously stored settings run the VistaCam PC Footswitch configuration program as follows:
   a. Double click on the VistaCam PC FS Interface icon in the desktop, or
   b. Click on the Start button.
   c. Click on Programs.
   d. Click on VistaCam PC FS Interface.
   e. Click on VistaCam PC FS Interface.
   f. Click on the RECALL button.
   g. Click on the program name that you previously saved (from the list that pops up).
   h. Click the CONFIGURE button.
   i. The VistaCam Multi-function Footswitch is now configured and ready to work with the program functions that you previously saved and recalled.

FIG. 3 is a chart which illustrates the sample keystroke commands associated with the switches 34–42 on the foot switch 30 and the equivalent function of a keyboard entry for the aforementioned dental programs Dentrix, Eaglesoft, and Vipersoft. The program for the footswitch interface which permits the duplication of equivalent keyboard functions is set forth hereafter. The illustrations following the program are illustrative of the foot switch functions equivalent to the keyboard entry.

While the foot switch 30 has been described with respect to functions associated with dental imaging, the same program and interface can be utilized such that the foot switch could be operational with other computer programs. For example, if one were operating with a spread sheet data base in which certain data were to be compared with other data in the spread sheet or certain mathematical functions undertaken with respect to the data, the program could be modified to have switch 34 through 42 undertake certain mathematical computations such as addition, substraction, multiplication, division or comparisons with respect to the data.

The footswitch interface and software may also be applied to other applications in the general medical field where a computer is integral to the medical procedure or diagnostic and there is the need to prevent cross-contamination or asepsis.

While the present invention has been described with respect to the exemplary embodiments thereof, it will be manifest to those of ordinary skill in the art that certain modifications and changes may be made without departing from the spirit and scope of the invention. Therefore it is manifestly intended that the invention be limited only by the scope of the claims and the equivalence thereof.

We claim:
1. A foot switch for hands off operation of a computer imaging system comprising:

a programmed central processing unit;

a keyboard;

a viewing screen;

an image source;

a programmable foot switch having a plurality of foot activatable switch members, each of said foot activatable switch members programmed to perform the equivalent of keyboard functions by foot manipulation in order to operate said programmed central processing unit, each of said foot switch members programmable with up to 24 keystroke commands for manipulation, viewing and storage of intra-oral images;

an interface disposed between said foot switch and said programmed central processing unit permitting the parallel connection of said foot switch and said keyboard to said programmed central processing unit.

2. A foot switch in accordance with claim 1 wherein said foot switch comprises five switch members independently operable.

3. A foot switch in accordance with claim 1 wherein said image source is an image stored in said programmed central processing unit.

4. A foot switch in accordance with claim 1 wherein said imaging source is a manually operated camera.

5. A foot switch for a computer imaging system allowing foot operation of the computer imaging system, said foot switch comprising a housing member having positioned thereon, a plurality of foot activatable switch members, each of said foot activatable switch members programmable to perform the equivalent of keyboard functions by foot manipulation, each of said switch members stores up, to 24 keystroke commands, said foot switch in communication with a programmed central processing unit.

6. A foot switch in accordance with claim 5 wherein said plurality of switch members comprises five independently operable switch members.

7. A foot switch in accordance with claim 6 wherein said switch members are activatable by depressing said switch member.

8. A method of hands off operation of a computer imaging system comprising a programmed central processing unit, viewing screen, image source, and keyboard, said method comprising:

positioning an interface between said keyboard and said programmed central processing unit;

connecting a programable foot switch to said interface, said programmable foot switch having a plurality of foot activatable switch members, each of said foot activatable switch members programmable to perform the equivalent of keyboard functions by foot manipulation in order to operate said programmed central processing unit, each of said foot switch members programmable with up to 24 keystroke commands for manipulation, viewing and storage of intra-oral images;

programming each of said plurality of foot activatable switch members with the desired keystroke functions for operation of the programmed central processing unit.

* * * * *